US005453544A

United States Patent [19]
Giacobbe

[11] Patent Number: 5,453,544
[45] Date of Patent: Sep. 26, 1995

[54] PROCESS FOR MAKING TERTIARY-THIOLS

[75] Inventor: Thomas J. Giacobbe, Skillman, N.J.

[73] Assignee: Mobil Oil Corporation, Fairfax, Va.

[21] Appl. No.: 254,624

[22] Filed: Jun. 6, 1994

[51] Int. Cl.[6] .................................................. C07C 319/04
[52] U.S. Cl. .................................................................. 568/72
[58] Field of Search .......................................... 568/72

[56] References Cited

U.S. PATENT DOCUMENTS

| | | | |
|---|---|---|---|
| 2,386,769 | 10/1945 | Badertscher et al. | 260/609 |
| 2,434,510 | 1/1948 | Olin et al. | 260/609 |
| 2,464,049 | 3/1949 | Mikeska | 260/609 |
| 2,502,596 | 4/1950 | Schulze | 260/609 |
| 2,610,981 | 9/1952 | Short | 260/609 |
| 2,950,324 | 8/1960 | Loev et al. | 260/609 |
| 2,951,875 | 9/1960 | Loev et al. | 260/609 |
| 3,247,195 | 4/1966 | Kerr | 260/242 |
| 3,702,886 | 11/1972 | Argauer et al. | 423/328 |
| 3,832,449 | 8/1974 | Rosinski et al. | 423/328 |
| 4,102,931 | 7/1978 | Buchholz | 260/609 |
| 4,582,939 | 4/1986 | Perozzi et al. | 568/72 |
| 4,638,093 | 1/1987 | Fried | 568/73 |
| 4,891,445 | 1/1990 | Arretz | 568/72 |
| 4,954,325 | 9/1990 | Rubin et al. | 423/328 |

Primary Examiner—Johann Richter
Assistant Examiner—John Peabody
Attorney, Agent, or Firm—Alexander J. McKillop; Malcolm D. Keen; Charles A. Malone

[57] ABSTRACT

A process for making t-butylthiol by reacting hydrogen sulfide and an olefin having a carbon number of 3 to 15 in the presence of a HZSM-5, HZSM-12, or MCM-22 zeolite catalyst. The reaction takes place under autogenous pressure conditions and a temperature of about 70° C. to about 160° C.

10 Claims, 1 Drawing Sheet

PROCESS FOR MAKING TERTIARY-THIOLS

FIELD OF THE INVENTION

This invention relates to the preparation of tertiary thiols by reacting hydrogen sulfide with $C_3$ to $C_{15}$ olefins in the presence of a microporous crystalline catalyst.

BACKGROUND OF THE INVENTION

It is known in the prior art that thiols (mercaptans) can be prepared in a process which comprises the addition of hydrogen sulfide to olefins, particularly in the presence of a catalyst, most particularly an acid catalyst. It is further recognized that this process has been applied almost exclusively to the production of tertiary thiols. Markovniokov addition of $H_2S$ to a "tertiary" olefin, usually an olefin polymer such as a propylene or butylene trimer or tetramer, results in near quantitative selectivity to the tertiary thiol. Exemplification of tertiary thiol preparation from $H_2S$ and tertiary olefin in the presence of an acidic catalyst is provided by U.S. Pat. Nos. 2,386,769, 2,434,510, 2,464,049, 2,502,596, 2,610,981, 2,950,324, 2,951,875 and 4,102,931.

Certain heterogenous acid catalysts (non-zeolites) including alumina, acid on silica and sulfonic acid exchange resins also convert olefins to thiols. These catalysts are disclosed in U.S. Pat. Nos. 2,951,875, 2,950,324, and 4,582,939 which issued to Goshorn et al., Goshorn et al., and Papay et al. respectively.

X and Y zeolites, and aluminosilicates with FAU structures are used to make tertiary thiols from hydrogen sulfide and an olefin. A method for manufacturing tertiary mercaptans where zeolites are utilized is disclosed in U.S. Pat. No. 4,102,931 that issued to Bucholz.

U.S. Pat. No. 4,638,093 which issued to Fried on Jan. 20, 1987 discloses a process for the preparation of secondary thiols by the addition of $H_2S$ to $C_{10}$ to $C_{30}$ linear olefins in the presence of certain zeolite catalysts. The process achieves high selectivity to the secondary thiol and minimizes formation of dialkyl sulfide by-products. The secondary thiol products are of particular advantage for use as intermediates in the preparation of surfactant chemicals.

Nothing disclosed in the prior art teaches the use of MCM-22, HZSM-5, OR HZSM-12 catalysts for making tertiary thiols. Also, there is nothing in the prior art which would suggest that other acidic zeolites will be useful in making tertiary thiols. Examples of acidic zeolites which will not catalyze a reaction of hydrogen sulfide and isobutylene to make t-butylmercaptan include Chabazite, Erionite, ZK-5 and Rho. ZK-5 zeolite is disclosed in U.S. Pat. No. 3,247,195 which issued to Kerr on Apr. 19, 1966.

Therefore, what is needed is a method for making tertiary thiols with MCM-22, HZSM-5, or HZSM-12 catalysts in the presence of hydrogen sulfide and olefins e.g. isobutylene so as to obtain substantially quantitative yields of tertiary thiols.

SUMMARY OF THE INVENTION

This invention is directed to a process for making tertiary thiols. In the practice of this invention, an olefin having a carbon number in the range from about 3 to about 15 is reacted with hydrogen sulfide in the presence of a microporous crystalline catalyst. The preferred catalysts comprise MCM-22, HZSM-5, and HZSM-12. Isobutylene is the preferred olefin. The reaction takes place under autogenous pressure conditions at a temperature of from about 70° C. to about 160° C. The preferred temperature is about 90° C.

It is therefore an object of this invention to provide a quantitative process for making tertiary thiols with no significant waste production.

It is another object of this invention to provide for an economical process for making tertiary thiols.

It is a further object of this invention to provide for a method of producing tertiary thiols which can be used as an economical raw material for making gear oil lubricants.

DESCRIPTION OF THE PREFERRED EMBODIMENTS

Figure 1:
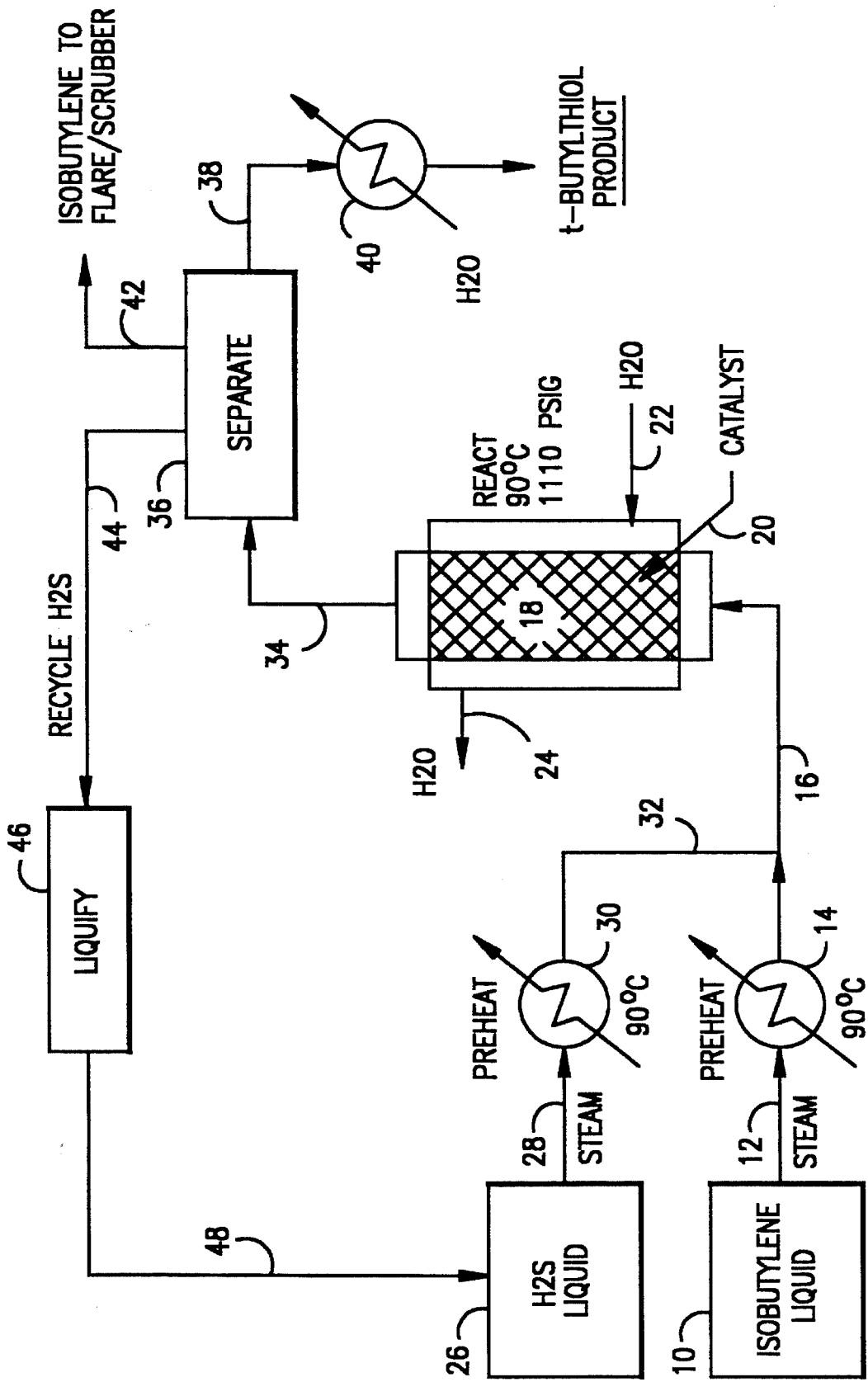
FIG. 1 is a block process diagram of a preferred embodiment for making t-butylthiol from hydrogen sulfide and isobutylene.

In the practice of this invention, tertiary thiols, and more specifically and as preferred, t-butylthiol is prepared in a continuous process using isobutylene, excess hydrogen sulfide and a zeolite catalyst (e.g. HZSM-5, HZSM-12, or MCM-22). A method for making tertiary mercaptans where zeolites are utilized is disclosed in U.S. Pat. No. 4,102,931 which issued to Buchholz. This patent is incorporated by reference herein. Unreacted excess hydrogen sulfide is recycled in the subject continuous process. Details of the process are as follows.

PREPARATION OF t-BUTYLTHIOL FROM ISOBUTYLENE

1. CHEMISTRY

One mole of isobutylene and 1.5 mole hydrogen sulfide (0.5 mole excess) react in the presence of a HZSM-5 zeolite catalyst at 90° C. and autogenous pressure to produce t-butylthiol. Unreacted $H_2S$ is recovered from the reaction product and recycled. The liquid product is polish filtered and sent to storage.

The following equation represents the reaction:

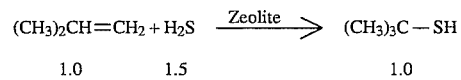

Mole    1.0      1.5      1.0

Reactant Mole Ratio
$H_2S/C_4H_8=1.5$
Catalyst Loading=20 g/106 g reaction mixture
Final Product t-butylthiol→100% (By GC)
Product Yield Based on total $H_2S+C_4H_8=84$ wt. % (one third of $H_2S$ is recycled)

2. PROCESS CONDITIONS

Reaction: Temperature=194° F.
Pressure=1,110psig

Although isobutylene is used in the process above, any olefin having a carbon number in the range from about 3 to about 15 can be utilized. The preferred catalysts for use herein comprise a MCM-22, HZSM-5, or HZSM-12 and mixtures thereof. Isobutylene is the preferred olefin. The reaction takes place under autogenous pressure conditions at a temperature of from about 70° C. to about 160° C. The preferred temperature is about 90° C.

Zeolites HZSM-5, HZSM-12, and MCM-22 are disclosed in U.S. Pat. Nos. 3,702,886, 3,832,449, and 4,954,325 respectively. These patents are incorporated by reference herein.

A process for making t-butylthiol is set forth in a blocked diagram shown in FIG. 1. As is shown in FIG. 1, hydrogen sulfide is directed from a hydrogen sulfide storage vessel 26 whereupon it flows by conduit 28 into a heat exchanger 30 where it is preheated to a temperature of about 90° C. Thereafter, the heated hydrogen sulfide is removed from the heat exchanger 30 via conduit 32 and is directed into line 16 where it mixes with heated isobutylene liquid. Heated isobutylene is obtained from preheater 14 where it is heated by steam to a temperature of about 90° C. Isobutylene liquid is obtained from vessel 10 where it flows via conduit 12 into heat exchanger 14 for heating to a temperature of about 90° C. Upon mixing with heated hydrogen sulfide, isobutylene liquid flows via conduit 16 into the bottom of reactor 18 which contains catalyst 20. Here it is reacted at a temperature of 90° C. and a pressure of 1,110 psig for a time sufficient to obtain the desired reaction product of mixed t-butylthiol.

Water is directed via conduit 22 around reactor 18 so as to maintain the temperature as desired. The cooling water is removed from the reactor 18 via conduit 24. Reactants are removed from reactor 18 via conduit 34 where they are directed into separator 36. Unreacted hydrogen sulfide gas is separated from the other reactants in separator 36 and removed therefrom via conduit 44 where it is directed into liquifier 46. Here it is converted to a liquid state. Thereafter, liquified hydrogen sulfide is removed from liquefier 46 via conduit 48 and directed into liquid hydrogen sulfide vessel 26 for further utilization in the process. Unreacted isobutylene is removed from separator 36 via conduit 42 and sent to a scrubber where products harmful to the environment are removed. Scrubbed isobutylene is thereafter flared. T-butylthiol is removed from separator 36 via conduit 38 and directed into heat exchanger 40 where it is cooled by water and subsequently sent to storage.

Catalyst Sources

HZSM-5 was obtained from Mobil as HZSM 5B extrudate, HZSM-12 and MCM-22 were obtained from Mobil Research and Development Corp., Paulsboro, N.J. Y. Zeolite "OCTACAT Y" was obtained from Davison. These catalysts were calcined at 530° C. for 14 hours and then stored in a desiccator prior to use. "AMBERLYST 15", a sulfonic acid resin catalyst, was purchased from Aldrich Chemical.

t-Butylthiol: General Procedure For Preparation (a) The equipment: A 300 mL, 316 stainless steel pressure reactor (Autoclave Engineers) was fitted with a vent line, rupture disk (2,048 psi), thermowell, turbine agitator and liquid feed line. Reaction temperature was monitored using a thermocouple in the thermowell and maintained using a controller and electrical heater. The liquid feed line was connected to a liquified-gas delivery system that metered liquid from a calibrated Jurgensen gauge. The Jurgensen gauge was fitted with a pressure relief valve set at 1,500 psi and a high pressure nitrogen gas supply. Nitrogen gas pressure supplied the motive force to transfer liquids from the Jurgensen gauge into the reactor. The reactor vent line was connected sequentially to a 1,000 mL stainless steel liquid knock-out vessel and a hydrogen sulfide trapping system. This trapping system contained primary and secondary scrubbers and an activated carbon absorption bed. The primary scrubber was a 4,000 mL stirred vessel fitted with a stainless steel dip tube, and it contained a solution made from sodium hydroxide pellets (300 g) dissolved in 3,000 mL of aqueous sodium hypochlorite (5 wt %). The secondary scrubber was a 1,000 mL vessel fitted with a fitted glass dip tube, and it too contained 800 mL of the same solution made from caustic pellets and aqueous sodium hypochlorite. The absorption bed was a one gallon container with dip tube and it opened to the atmosphere. The absorption bed was filled with activated carbon containing 12 wt % cupric oxide "(SULFASORB 12", 4×10 mesh, Calgon) The aqueous scrubber solutions were changed after each batch. Using this scrubbing system, hydrogen sulfide was never detected escaping to the atmosphere.

(b) The procedure: The reactor was charged with zeolite catalyst (20 g; calcined) sealed, atmosphere exchanged for nitrogen gas and tested for leaks. Liquid hydrogen sulfide (51 g, 66 mL, density taken as 0.774 g/mL, 1.5 mole) was charged from the Jurgensen gauge into the reactor. The reactor was stirred at 300 rpm with a 6-blade turbine agitator and heated to 90° C. Isobutylene (56 g, 94.9 mL, density taken as 0.59 g/mL, 1 mole) was slowly added over 2–3 hours to the heated reactor. The reaction was very exothermic. After completing isobutylene addition, the reactor was maintained at 90° C. and the pressure was monitored. Typically, reactor pressure fell from 900 psig (pressure before isobutylene addition) until reaching a plateau at 260 psig in about 2 hours. The reactor was maintained at the plateau pressure for at least 4 hours before cooling to room temperature. Excess hydrogen sulfide was slowly vented to the scrubber system. The reactor was opened and the contents, a water-white liquid with suspended catalyst therein, was removed. The catalyst was collected by filtration. The liquid was analyzed by gas chromatography (GC), to detect unreacted isobutylene (dissolved in the t-butylthiol), and to determine t-butylthiol purity. Typically, isobutylene was not detected, only t-butylthiol.

Gas Chromatography

Gas chromatography was done on a Shimadzu GC-9A fitted with a 30 meter by 0.25 mm ID WCOT fused silica column with 0.25 micrometer coated with SP 2100 (Supelco catalog number 2-4007M). Injection was split, and the oven was programmed. The initial temperature was 60° C. which was held for 2 minutes and then heated at 15° C./min until reaching 250° C. where it was maintained for 20 minutes. Injection port temperature was maintained at 250° C. A FID detector was utilized.

The elution times of t-butylthiol and toluene were 3.2 and 5.0 minutes respectively. Toluene was used as an internal standard. Tert-butylthiol was purchased from Aldrich Chemical and used as reference to get a response factor relative to toluene (typically about 0.54). The response factor was non-linear. It varied depending upon injection size. Using repeated injections of the same size kept the error limit at about ±2%. This large error limit resulted from using a FID detector for a compound with high weight-percent sulfur (35 wt %).

TABLE 1

| t-BUTYLTHIOL: ZEOLITE CATALYZED REACTIONS OF ISOBUTYLENE AND HYDROGEN SULFIDE | | |
|---|---|---|
| | PURITY t-BUTYLTHIOL $H_2S$: Isobutylene Mole Ratio | |
| CATALYST | 0.75:1 | 1.5:1 |
| Exploratory Experiments | | |
| HZSM-5 | 59 | 99 |
| HZSM-12 | 44 | 99 |

TABLE 1-continued t-BUTYLTHIOL: ZEOLITE CATALYZED REACTIONS
OF ISOBUTYLENE AND HYDROGEN SULFIDE

| CATALYST | PURITY t-BUTYLTHIOL H₂S: Isobutylene Mole Ratio | |
|---|---|---|
| | 0.75:1 | 1.5:1 |
| MCM-22 | 44 | 99 |
| Control Experiments | | |
| "AMBERLYST 15" | 78 | 97 |
| "OCTACAT Y" | 65 | 99 |

*Hydrogen sulfide and catalyst were mixed at room temperature in autoclave and then heated to 90° C. Isobutylene was slowly added over 2–3 hours. Reaction terminated after pressure dropped and remained constant.

An analysis of the above results indicate that changing the stoichiometry and using an excess of isobutylene markedly lowers t-butylthiol yields. Also, these results indicate that HZSM-5, HZSM-12 and MCM-22 catalyzed the reaction of isobutylene and hydrogen sulfide to make t-butylthiol in yields approaching quantitative with a substantially high purity.

Although the present invention has been described with preferred embodiments, it is to be understood that modifications and variations may be resorted to without departing from the spirit and scope of this invention as those skilled in the art will readily understand. Such Aldrich Chemical and used as reference to get a response factor relative to toluene (typically about 0.54). The response factor was non-linear. It varied depending upon injection size. Using repeated injections of the same size kept the error limit at about ±2%. This large error limit resulted from using a FID detector for a compound with high weight-percent sulfur (35 wt %).

TABLE 1 t-BUTYLTHIOL: ZEOLITE CATALYZED REACTIONS
OF ISOBUTYLENE AND HYDROGEN SULFIDE

| CATALYST | PURITY t-BUTYLTHIOL H₂S: Isobutylene Mole Ratio | |
|---|---|---|
| | 0.75:1 | 1.5:1 |
| Exploratory Experiments | | |
| HZSM-5 | 59 | 99 |
| HZSM-12 | 44 | 99 |
| MCM-22 | 44 | 99 |
| Control Experiments | | |
| "AMBERLYST 15" | 78 | 97 |
| "OCTACAT Y" | 65 | 99 |

*Hydrogen sulfide and catalyst were mixed at room temperature in autoclave and then heated to 90° C. Isobutylene was slowly added over 2–3 hours. Reaction terminated after pressure dropped and remained constant.

An analysis of the above results indicate that changing the stoichiometry and using an excess of isobutylene markedly lowers t-butylthiol yields. Also, these results indicate that HZSM-5, HZSM-12 and MCM-22 catalyzed the reaction of isobutylene and hydrogen sulfide to make t-butylthiol in yields approaching quantitative with a substantially high purity.

Although the present invention has been described with preferred embodiments, it is to be understood that modifications and variations may be resorted to without departing from the spirit and scope of this invention as those skilled in the art will readily understand. Such modifications and variations are considered to be within the purview and scope of the appended claims.

What is claimed:

1. A process for making tertiary thiols comprising:
    reacting an olefin having a carbon number from 3 to 15 with hydrogen sulfide in the presence of a zeolite catalyst select from a member of the group consisting of HZSM-5, HZSM-12, and MCM-22 under autogenous pressure conditions and a temperature of about 70° C. to about 160° C. in an amount and for a time sufficient to obtain substantially pure tertiary thiols.

2. The process as recited in claim 1 where the olefin is isobutylene.

3. The process as recited in claim 1 where the mole ratio of hydrogen sulfide to olefin is 1.5:1.

4. The process as recited in claim 1 where the olefin is isobutylene and the mole ratio of hydrogen sulfide to isobutylene is 1.5:1, the temperature is 90° C. and the t-butylthiol purity is 99 wt. %.

5. A process for making t-butylthiols comprising:
    reacting isobutylene with hydrogen sulfide in the presence of a zeolite catalyst selected from a member of the group consisting of HZSM-5, HZSM-12, and MCM-22 under autogenous pressure conditions and a temperature of about 70 degrees C. to about 160 degrees C. in an amount and for a time sufficient to obtain substantially pure t-butylthiols.

6. The process as recited in claim 5 where the mole ratio of hydrogen sulfide to olefin is 1.5:1.

7. The process as recited in claim 5 where the zeolite is HZSM-5 and the mole ratio of hydrogen sulfide to isobutylene is 1.5:1, the temperature is 90° C. and the t-butylthiol purity is 99 wt. %.

8. A process for making t-butylthiols comprising:
    reacting isobutylene with hydrogen sulfide in the presence of a zeolite HZSM-5 catalyst selected under autogenous pressure conditions and a temperature of about 70 degrees C. to about 160 degrees C. in an amount and for a time sufficient to obtain substantially pure t-butylthiols.

9. The process as recited in claim 8 where the mole ratio of hydrogen sulfide to olefin is 1.5:1.

10. The process as recited in claim 8 where the mole ratio of hydrogen sulfide to isobutylene is 1.5:1, the temperature is 90° C. and the t-butylthiol purity is about 99 wt. %.

* * * * *